(12) United States Patent
Neumann

(10) Patent No.: US 11,854,684 B2
(45) Date of Patent: Dec. 26, 2023

(54) METHODS AND SYSTEMS FOR NOURISHMENT REFINEMENT USING PSYCHIATRIC MARKERS

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 0 days.

(21) Appl. No.: 17/136,120

(22) Filed: Dec. 29, 2020

(65) Prior Publication Data

US 2022/0208339 A1 Jun. 30, 2022

(51) Int. Cl.
*G16H 20/60* (2018.01)
*G16H 50/50* (2018.01)
(Continued)

(52) U.S. Cl.
CPC .............. *G16H 20/60* (2018.01); *A61B 5/16* (2013.01); *G06F 16/242* (2019.01); *G06F 16/24575* (2019.01); *G06N 20/00* (2019.01); *G16H 10/20* (2018.01); *G16H 10/60* (2018.01); *G16H 20/70* (2018.01); *G16H 50/20* (2018.01); *G16H 50/30* (2018.01); *G16H 50/50* (2018.01); *G16H 50/70* (2018.01); *A61B 5/0042* (2013.01);
(Continued)

(58) Field of Classification Search
CPC ........ G16H 20/60; G16H 50/20; G16H 50/70; G16H 50/50; G16H 20/70; G16H 50/30; G16H 10/60; G16H 10/20; A61B 5/16; A61B 5/369; A61B 5/082; A61B 6/037; A61B 5/0042; A61B 5/055; G06F 16/242; G06F 16/24575; G06N 20/00
See application file for complete search history.

(56) References Cited

U.S. PATENT DOCUMENTS

| 2002/0155170 A1 | 10/2002 | Walsh |
| 2006/0062859 A1 | 3/2006 | Blum |

(Continued)

OTHER PUBLICATIONS

Cerasa et al. "Personality Biomarkers of Pathological Gambling: A Machine Learning Study." Journal of Neuroscience Methods, vol. 294, 2018, pp. 7-14, https://doi.org/10.1016/j.jneumeth.2017.10.023 (Year: 2018).*

(Continued)

*Primary Examiner* — Peter H Choi
*Assistant Examiner* — Chad A Newton
(74) *Attorney, Agent, or Firm* — CALDWELL INTELLECTUAL PROPERTY LAW

(57) ABSTRACT

A system for nourishment refinement using psychiatric markers includes a computing device designed and configured to retrieve a psychiatric marker relating to a user, identify a nutrient variation as a function of the psychiatric marker, establish nourishment possibilities as a function of the nutrient variation, and generate a nourishment program, wherein generating further includes training a machine learning process as a function of a training set relating psychiatric markers and nutrient variations to nourishment programs, and generating the nourishment program as a function of the psychiatric marker, the nourishment possibilities, and the machine-learning process.

16 Claims, 8 Drawing Sheets

(51) Int. Cl.
*G16H 50/20* (2018.01)
*G16H 20/70* (2018.01)
*G16H 50/30* (2018.01)
*G16H 10/20* (2018.01)
*G16H 50/70* (2018.01)
*G06F 16/242* (2019.01)
*G06F 16/2457* (2019.01)
*G06N 20/00* (2019.01)
*A61B 5/16* (2006.01)
*G16H 10/60* (2018.01)
*A61B 5/00* (2006.01)
*A61B 5/369* (2021.01)
*A61B 5/055* (2006.01)
*A61B 6/03* (2006.01)
*A61B 5/08* (2006.01)

(52) U.S. Cl.
CPC ............... *A61B 5/055* (2013.01); *A61B 5/082* (2013.01); *A61B 5/369* (2021.01); *A61B 6/037* (2013.01)

(56) References Cited

U.S. PATENT DOCUMENTS

| | | |
|---|---|---|
| 2008/0221932 A1 | 9/2008 | Kane |
| 2009/0264520 A1 | 10/2009 | Bhagat |
| 2010/0021533 A1 | 1/2010 | Mazed |
| 2011/0189161 A1 | 8/2011 | Blum |
| 2012/0282592 A1* | 11/2012 | Kawamura ........ G01N 33/6893 204/451 |
| 2013/0218602 A1 | 8/2013 | Lahteenmaki |
| 2013/0261183 A1 | 10/2013 | Bhagat |
| 2017/0000856 A1 | 1/2017 | Holstein |
| 2018/0025368 A1* | 1/2018 | Frank ................. G06Q 30/02 705/7.29 |
| 2019/0126039 A1* | 5/2019 | Yoo ..................... A61N 1/3603 |
| 2019/0178900 A1 | 6/2019 | Smith |
| 2019/0231240 A1* | 8/2019 | Short ................... G09B 19/00 |
| 2020/0138362 A1 | 5/2020 | Koumpan |
| 2020/0348319 A1 | 11/2020 | Smith |

OTHER PUBLICATIONS

Munro et al. "Using Personality as a Predictor of Diet Induced Weight Loss and Weight Management." International Journal of Behavioral Nutrition and Physical Activity, vol. 8, No. 1, 2011, https://doi.org/10.1186/1479-5868-8-129 (Year: 2011).*
Ttile: Impact of diet on adult hippocampal neurogenesis; By: Thruet & Stangl; Date: Dec. 2009.
Title: Integrated medical care management and behavioral risk factor reduction for multicondition patients: behavioral outcomes of the TEAMcare trial; Date: Nov. 4, 2013; by: Dori Rosenberg.
Title: Study of Diet Recommendation System based on Fuzzy Logic and Ontology; by: Chavan, Date: Dec. 12, 2015.
Title: Effects of a Personalized Intervention Program on the Biochemical and Hematological Profile in Community Dwelling Old Adults—The AGA@4life Intervention Model; Date: Jan. 22, 2020; by: Armando Caseiro.

* cited by examiner

| Physical Measurement | Subjective Response |
|---|---|
| C reactive protein | Nervous |
| Brain derived neurotrophic factor | On edge |
| Apolipoprotein C3 | Restless |
| Epidermal growth factor | Unsettled |
| Cortisol | Stressed |
| Resistin | Surprised |
| Prolactin | Creative |
| Myeloperoxidase | Imaginative |
| Insulin-derived growth factors | Daring |
| Malondialdehyde (MDA) | Adventurous |
| Urinary isoprostranes | High energy |
| Ethylene | Angry |
| Norepinephrine | Calm |
| Monoamine oxidase | Comfortable |
| Zinc | Contentment |
| N1-acetyltransferase | Peace |
| Creatinine | Relaxed |
| Potassium | Loveable |
| Tau protein | Mood intesnity |
| Macrophage migration inhibitory factor | Exercise |
| CYP2D6 genes | Medication |
| Dopamine | Sleep |
| Serotonin | Irritability |
| Glutamate | Impulsivity |
| Histamine | Dullness |
| Epinephrine | Obsessing |
| Gamma aminobutyric acid (GABA) | Slow moving |

*FIG. 4*

| 108 | 116 | 128 | 504 | 508 | 512 | 516 |
|---|---|---|---|---|---|---|
| Psychiatric Marker | Nutrient Variation | Nourishment Program Day 1 | Breakfast | Lunch | Dinner | Snack |
| Low serotonin | Eggs, cheese, pineapple, tofu, salmon, turkey | Breakfast B; Lunch A; Dinner C; Snack B | A. Steel cut oatmeal with mixed berries | A. Turkey sandwich | A. Lentil stew | A. Vegetable crudites |
| | | | B. Frittata with goat cheese and pesto | B. Greek salad with grilled chicken | B. Moroccan chicken | B. Cheese stick |
| | | | C. Peach mint smoothie | C. Shrimp and avocado ceviche | C. Broiled salmon over jasmine rice | C. Trail mix |

METHODS AND SYSTEMS FOR NOURISHMENT REFINEMENT USING PSYCHIATRIC MARKERS

FIELD OF THE INVENTION

The present invention generally relates to the field of artificial intelligence. In particular, the present invention is directed to methods and systems for nourishment refinement using psychiatric markers.

BACKGROUND

Nourishment selection can be challenging, particularly when coupled with unknown interactions and requirements affect nutritional needs. This can be further hampered by massive quantities of nourishment options available.

SUMMARY OF THE DISCLOSURE

In an aspect, a system for nourishment refinement using psychiatric markers, the system comprising a computing device designed and configured to retrieve a psychiatric marker relating to a user; identify a nutrient variation as a function of the psychiatric marker; establish nourishment possibilities as a function of the nutrient variation; and generate a nourishment program, wherein generating further comprises training a machine learning process as a function of a training set relating psychiatric markers and nutrient variations to nourishment programs; and generating the nourishment program as a function of the psychiatric marker, the nourishment possibilities, and the machine learning process.

In an aspect, A method of nourishment refinement using psychiatric markers, the method comprising retrieving, by a computing device, a psychiatric marker relating to a user; identifying, by the computing device, a nutrient variation as a function of the psychiatric marker; establishing, by the computing device, nourishment possibilities as a function of the nutrient variation; and generating by the computing device, a nourishment program, wherein generating further comprises training a machine learning process as a function of a training set relating psychiatric markers and nutrient variations to nourishment programs; and generating the nourishment program as a function of the psychiatric marker, the nourishment possibilities, and the machine learning process.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 4 is a table illustrating an exemplary embodiment of psychiatric markers;

FIG. 5 is a table illustrating an exemplary embodiment of a nourishment program;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for nourishment refinement using psychiatric markers. In an embodiment, a psychiatric marker relating to a user aids in identifying a nutrient variation. A computing device establishes nourishment possibilities using the nutrient variation and generates a nourishment program. A nourishment program may aid in the prevention, treatment, and/or reversal of a psychiatric disorder.

Figure 1:
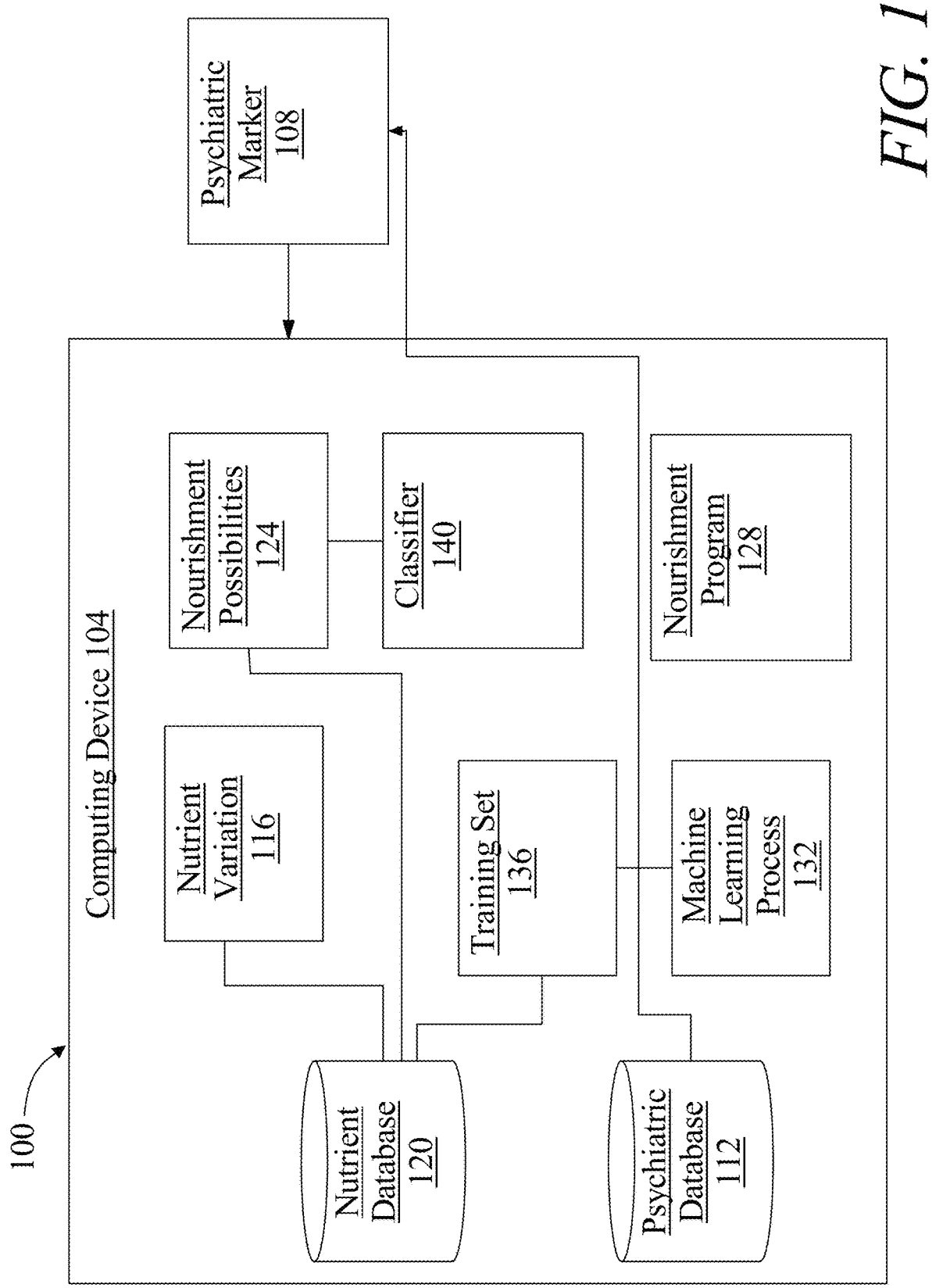
FIG. 1 is a block diagram illustrating an exemplary embodiment of a system for nourishment refinement using psychiatric markers.

Referring now to the drawings, FIG. 1 illustrates an exemplary embodiment of a system 100 for nourishment refinement using psychiatric markers. System 100 includes a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any possibilities thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1. computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to retrieve a psychiatric marker 108 relating to a user. A "psychiatric marker," as used in this disclosure, is an indicator of a psychiatric process, a psychiatric condition, a psychiatric disease, a predisposition to develop a psychiatric condition and/or a psychiatric disease, and/or risk of developing a future psychiatric condition, and/or disease. A psychiatric marker 108 may include one or more physical measurements. A "physical measurement," as used in this disclosure, is a psychiatric marker obtained from a physiological extraction. A physiological extraction may be obtained from a biofluid and/or specimen such as but not limited to a blood sample, a saliva sample, a urine sample, a stool sample, a hair sample, a tissue sample, a skin sample, a nail sample, a fixed and/or stained slide containing a human component such as a cervical sample and the like. A physiological extraction may be obtained from one or more blood components, including but not limited to peripheral blood, umbilical cord blood, serum blood, plasma blood, buffy coat blood and the like. A physiological extraction may be obtained from human primary cells derived from human bio samples, A physiological extraction may be obtained from deoxyribonucleic acid (DNA), ribonucleic acid (RNA), and/or any component of genetic material including but not limited to a gene, and/or a group of genes. A physiological extraction may be obtained from one or more cells of the human body, such as for example a stem cell. For instance and without limitation, a psychiatric marker 108 may include, but is not limited to alpha 1 anti-trypsin, brain derived neurotrophic factor (BDNF), spermidine, N1-acetyltransferase 1, c-reactive protein, Interleukin-6 (IL-6), tumor necrosis factor alpha (TNF-alpha), alpha1 antitrypsin, apolipoprotein C3, epidermal growth factor, cortisol, resistin, prolactin, myeloperoxidase, soluble tumor-necrosis factor alpha receptor type 2, cytokines, brain derived growth factors, insulin derived growth factors, glial marker SB 100, malondialdehyde (MDA), urinary isoprostranes, DNA methylation, miRNA regulation, ammonia, ethylene, norepinephrine, monoamine oxidase (MAO), 3-Methoxy-4-hydroxyphenylethylene glycol (MHPG), zinc, corticotrophin-releasing hormone (CRH), hippocampal volume, CSF-B amyloid, growth differentiation factor-15, hemopexin, hepsin, matrix metalloproteinase-7, retinol binding protein-4, trans thyretin, iron, beta-amyloid, tau, phosphor-tau, dopamine, serotonin, epinephrine, norepinephrine, glutamate, dopamine, gamma aminobutyric acid (GABA), histamine, 5-HIAA, glycine, phenylethylamine (PEA), 3,4-dihydroxyphenylacetic acid (DOPAC), homovanillic acid (HVA), normetanephrine, vanillylmandelic acid (VMA), creatinine, and the like. A psychiatric marker 108 may include findings and/or results from one or more procedures and/or diagnostic tests, including but not limited to magnetic resonance imaging (MRI), brain imaging, neuroimaging, electroencephalogram (EEG), position emission tomography (PET) scan, breath test, physical exam, neurological evaluation, neuroimaging, and the like.

With continued reference to FIG. 1, a psychiatric condition and/or a psychiatric disease may include but is not limited to neurodevelopment disorders such as autism spectrum disorder, attention deficit/hyperactivity disorder (ADHD), learning disorders, schizophrenia spectrum disorders such as schizophrenia, deficit subtype schizophrenia, nondeficit subtype schizophrenia, bipolar and related disorders, depressive disorders such as major depressive disorder, and/or premenstrual dysphoric disorder, anxiety disorders such as generalized anxiety disorder, panic disorder, and/or phobias, obsessive compulsive and related disorders such as obsessive compulsive disorder, hoarding disorder, and/or trichotillomania, trauma and stressor related disorders such as post-traumatic stress disorder (PTSD), and/or acute stress disorder, dissociative disorders such as dissociative identity disorder and/or dissociative amnesia, somatic symptom and related disorders such as somatic symptom disorder, illness anxiety disorder, and/or factitious disorder, feeding and eating disorders such as anorexia nervosa, bulimia, and/or binge eating disorder, elimination disorders such as enuresis, sleep-wake disorders such as insomnia, sleep apnea, and/or restless legs syndrome, sexual dysfunction such as premature ejaculation, and/or female orgasmic disorder, gender dysphoria, disruptive, impulse-control and conduct disorders such as kleptomania, and/or intermittent explosive disorder, substance related and addictive disorders such as excessive use of alcohol, caffeine, tobacco, drugs, and/or gambling disorder, neurocognitive disorders such as traumatic brain injury and/or Alzheimer's disease, personality disorders such as borderline personal disorder, and/or antisocial and narcissistic personality disorders, paraphilic disorders such as sexual sadism disorder, voyeuristic disorder, and/or pedophilic disorder, and/or other mental disorders.

With continued reference to FIG. 1, psychiatric marker 108 may include a subjective response. A "subjective response," as used in this disclosure, is a psychiatric marker based on and/or influenced by a user's personal feelings, tastes, emotions, and/or opinions. A subjective response may describe a user's current emotional state, such as for example by describing a user's moods. For instance, and without limitation, a subjective response may detail if a user feels nervous, on edge, restless, unsettled, stressed, surprised, creative, imaginative, daring, adventurous, high energy, low energy, angry, calm, comfortable, contentment, peace, relaxed, loveable, slow moving, fast moving, irritable, impulsive, dull, obsessing, and the like. A subjective response may describe a user's current mindset, mental state, emotional well-being, symptom control, symptom frequency, cognitive function, memory, recall, and the like. A subjective response may include a mental status examination such as to determine and evaluate a user's current state of mind through the domains of appearance, attitude, behavior, speech, mood, affect, thought process, thought content, perception, cognition, insight, and judgment. A subjective response may be determined using one or more assessment tools such as but not limited to Beck Depression Inventory for depression, Brief Psychiatric Rating Scale, Positive and Negative Syndrome Scale, Global Assessment of Functioning, and the like. In an embodiment, a subjective response may be administered by a third party such as but not limited to a psychiatrist, a nurse, a psychologist, an occupational therapist, a social worker, a license professional counselor, a physician, a pharmacist, and the like.

With continued reference to FIG. 1, computing device 104 may retrieve a psychiatric marker 108 from psychiatric database 112. Psychiatric database 112 may be implemented, without limitation, as a relational database, a key-value retrieval datastore such as a NOSQL database, or any other format or structure for use as a datastore that a person skilled in the art would recognize as suitable upon review of the entirety of this disclosure. Psychiatric database 112 may contain one or more entries containing one or more psychiatric markers 108 relating to a user.

With continued reference to FIG. 1, computing device 104 is configured to identify a nutrient variation 116 as a function of a psychiatric marker 108. A "nutrient variation," as used in this disclosure, is a list of one or more nutrients for which customization and/or optimization would be beneficial to psychiatric health of a user, based on a psychiatric marker 108. A "nutrient," as used in this disclosure, is a substance that provides nourishment for the growth and/or maintenance of life. A nutrient may include a vitamin, mineral, macromolecule, molecule, food, food group, ingredient, herb, spice, additive, superfood, edible, sustenance, refreshment and the like. For instance, and without limitation, a nutrient may include a macromolecule such as protein. In yet another non-limiting example, a nutrient may include an ingredient such as red bell pepper. Customization of a nutrient variation 116 may include identification of a quantity of a nutrient to avoid and/or eliminate. For instance, and without limitation, a psychiatric marker 108 that indicates a user has high levels of glutamate may be utilized to identify a nutrient variation 116 that customizes a nutrient such as oyster sauce and indicates that oyster sauce should be avoided because it contains high amounts of glutamate. Customization of a nutrient variation 116 may include a recommended quantity of a nutrient that may be safe for a user to consume. For instance, and without limitation, a nutrient variation 116 may specify that a user is recommended to consume no more than 4 ounces of red meat once per week. A nutrient variation 116 may contain a time constraint and may identify a nutrient that should only be consumed for a certain quantity of time. For instance, and without limitation, a nutrient variation 116 may specify that a user is recommended to consume ¼ of an avocado per day for a time period of two weeks. A nutrient variation 116 may identify one or more nutrients that may be recommended to be combined together and consumed in conjunction, to offer optimal nutritional effects. For instance, and without limitation, a nutrient variation 116 may recommend that a red bell pepper be consumed together in combination with spinach leaves, whereby the vitamin C in the red bell pepper may aid in the absorption of iron contained within the spinach leaves. A nutrient variation 116 may recommend one or more ingredients that may be contain a particular nutrient. For instance, and without limitation, a psychiatric marker 108 that indicates a user has low levels of serotonin, may be utilized by computing device 104 to identify one or more nutrients that aid in boosting levels of serotonin, including but not limited to salmon, poultry, eggs, spinach, seeds, milk, nuts, and soy products. Information pertaining to a nutrient variation 116 may be stored and contained within nutrient database 120. Nutrient database 120 may be implemented as any database suitable for use as psychiatric database 112 as described above in more detail.

With continued reference to FIG. 1, computing device 104 is configured to identify a nutrient variation 116 by determining a degree of psychiatric impairment. A "degree of psychiatric impairment," as used in this disclosure, is an indication as to how severe of a psychiatric condition and/or psychiatric illness that a user currently suffers from. Severity may be scored on a continuum, where for example if a user has no psychiatric illness and/or propensity for future psychiatric illness the user may have a very low degree of psychiatric impairment, whereby if for example a user has psychiatric illness that is currently being treated with outpatient medical appointments the user may have moderate psychiatric illness and whereby if the user is currently in a hospital and/or medical setting such as a psychiatric institution the user may have a high degree of psychiatric impairment. A degree of psychiatric impairment may also identify a user's compliance with any psychiatric treatment the user may be receiving, such as by indicating if the user takes any prescribed medications as directed and/or attends behavioral group therapy. A degree of psychiatric impairment may be obtained from information received from a user's medical records, self-reports, reports by family member, friends, and the like. A degree of psychiatric impairment may also be determined using a machine learning process, including any of the machine learning processes as described herein. In an embodiment, computing device 104 may receive training data containing a plurality of data entries correlating psychiatric markers to degrees of psychiatric impairment. Training data may be obtained from expert input, publicly available sources, previous iterations of generating a machine learning process and the like. Computing device 104 may train machine learning process using training data, to input a psychiatric marker relating to a user and output a degree of psychiatric impairment. A degree of psychiatric impairment may be utilized to identify a nutrient variation whereby for example, a user who has severe psychiatric impairment and is institutionalized may be at greater risk of having nutrient abnormalities whereby a user who has a low psychiatric impairment may not be at risk of having any nutrient abnormalities.

With continued reference to FIG. 1, a nutrient variation may be obtained using a machine learning process, including any of the machine learning processes as described herein. In an embodiment, computing device 104 may receive training data containing a plurality of data entries correlating psychiatric markers to nutrient variations. Training data may be received from expert input, publicly available sources, previous iterations of generating a machine learning process and the like. A machine learning process may be trained using training data, whereby the machine learning process may utilize a psychiatric marker 108 as an input and output a nutrient variation 116. This may be performed utilizing any methodology as described herein.

With continued reference to FIG. 1, computing device 104 may determine a psychiatric variation element and identify nutrient variation 116 as a function of the psychiatric variation element. A "psychiatric variation element," as used in this disclosure, is a substance that may alter and/or affect a person's psychiatric state. A psychiatric variation element may include a prescription medication, a vitamin, an herbal remedy, a homeopathic substance, a mineral, and the like. For instance, and without limitation, a psychiatric variation element may specify that a user consumes a substance such as a vitamin containing lithium orotate. Computing device 104 may identify a nutrient variation 116 as a function of the psychiatric variation element. For instance and without limitation, a psychiatric variation element that indicates a user consumes a prescription medication such as fluvoxamine may be utilized by computing device 104 to identify a nutrient variation 116 such as a restriction on the quantity of caffeine containing ingredients that a user may consume, including for example ingredients such as coffee, tea, ice cream, hot chocolate, dark chocolate and the like, due to the ability of fluvoxamine to enhance the side effects of caffeine. In yet another non-limiting example, a psychiatric variation element that indicates a user consumes an herbal remedy such as theanine to help with anxiety issues may be utilized by computing device 104 to identify a nutrient variation 116 to limit quantities of ingredients that naturally contain concentrated quantities of theanine, including for example, coffee, black tea, oolong tea, guarana, mate, swiss chard, sweet potato, kimchi, artichokes, eggs, shellfish, and parsley. A psychiatric variation element may be obtained from user input, retrieved from a medical record pertaining to the user, reported by a family member and/or friend of the user, and/or be obtained from a medical professional who may be treating and/or supervising care of the user.

With continued reference to FIG. 1, computing device 104 is configured to establish nourishment possibilities 124 as a function of a nutrient variation 116 and a degree of psychiatric impairment. A "nourishment possibility," as used in this disclosure, is an identification of a meal that complies with a nutrient variation 116. A meal may include any nourishment intended for human consumption, including but not limited to a breakfast, lunch, dinner, snack, and the like. In an embodiment, a roster of various nourishment possibilities 124 may be stored and contained within nutrient database 120. For instance, and without limitation, nourishment possibilities 124 may include a list of one or more meals that may be available to purchase from a food delivery company such as but not limited to GRUBHUB of Chicago, Illinois; DOORDASH of San Francisco, California; SEAMLESS of New York, New York; UBER EATS of San Francisco, California; INSTACART of San Francisco, California; POSTMATES of San Francisco, California; CHOWNOW of Los Angeles, California; WAITER.COM of Sunnyvale, California; MR. D FOOD of Cape Town, South Africa, and the like. In an embodiment, nourishment possibilities 124 may include one or more meals that may be available to purchase from a restaurant located within a certain geographical location of a user. This may be determined for example, based on a global positioning system (GPS) where a user is located, the longitude and/or latitude of where a user is located and the like. Computing device 104 may receive information regarding meals available for purchase by a local restaurant using any network methodology as described herein.

With continued reference to FIG. 1, computing device 104 may be configured to generate a query relating to a psychiatric marker 108 and nutrient variation 116 and establish nourishment possibilities 124 using the query. A "query," as used in this disclosure, is a datum used to retrieve nourishment possibilities 124. Retrieval may be affected by inputting the query into a data structure, database, and/or model, and receiving a corresponding output as a result. For instance, and without limitation, a psychiatric marker 108 indicating low dopamine levels in a user may be utilized by computing device 104 to generate a query to search for nourishment possibilities 124 that contain dopamine boosting foods such as milk, cheese, salmon, eggs, almonds, walnuts, and dark chocolate. In yet another non-limiting example, computing device 104 may utilize information contained within a nutrient variation 116 to generate a query relating to the nutrition and/or ingredients contained within nourishment possibilities 124. For instance, and without limitation, a nutrient variation 116 that contains a list of nutrients recommended for a user to consume in limited quantities may be utilized to generate a query to identify nourishment possibilities 124 that meet the requirements contained within the nutrient variation 116. For example, a nutrient variation 116 that contains a restriction for a user to consume very limited quantities of tyramine containing food products may be utilized to generate a query to locate nourishment possibilities 124 that contain foods that have limited quantities of tyramine.

With continued reference to FIG. 1, computing device 104 is configured to generate a nourishment program 128. A "nourishment program," as used in this disclosure, is an eating plan intended to treat, prevent, reverse, and/or cure psychiatric a psychiatric condition and/or a psychiatric disease. A nourishment program 128 may map out and identify meals that a user is recommend to consume. A nourishment program 128 may contain timing of meals and include one or more times when a user is recommended to consume a meal. For instance, and without limitation, a nourishment program 128 may recommend a user to consume breakfast on a Monday consisting of a yogurt parfait with fresh berries to be consumed at 8:00 am, while the nourishment program 128 may recommend a user to consume a spinach and tomato omelet on a Tuesday at 6:30 am. A nourishment program 128 may include one or more recommended snacks, such as a recommendation for a user to consume a handful of fresh walnuts at 3 pm on a Friday afternoon. A nourishment program 128 may be updated, and/or adjusted in real time, such as if computing device 104 may receive a new and/or more updated psychiatric marker 108, then computing device 104 may generate a more current nourishment program.

With continued reference to FIG. 1, computing device 104 generates nourishment program 128 by training a machine learning process 132 using a training set 136 relating psychiatric markers and nutrient variations to nourishment programs. A "machine learning process," as used in this disclosure, is a process that automatically uses training data to generate an algorithm that will be performed by computing device 104 to produce outputs given data provided as inputs; this is in contrast to a non-machine learning software program where the commands to be executed are determined in advance by a user and written in a programming language.

A machine learning process 132 may be trained using a training set 136. A "training set," as used in this disclosure is data containing correlations that a machine learning process may use to model relationships between two or more categories of data elements. For instance, and without limitation, training set 136 may include a plurality of data entries, relating psychiatric markers and nutrient variations to nourishment programs. Training set 136 may be obtained from one or more sources, including for example expert input, public forums, publications, and the like. Information pertaining to training set 136 may be contained within psychiatric database.

With continued reference to FIG. 1, computing device 104 may be configured to input a psychiatric marker 108 to a classifier 140. A "classifier," as used in this disclosure is a machine learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a process whereby a computing device 104 derives a classifier from training data. Classifier 140 may be trained using training data that may contain a plurality of data entries relating psychiatric markers to probable psychiatric conditions. Computing device 104 may train classifier 140 utilizing training data. Training data may be obtained from expert input, previous iterations of generating classifier 140, and/or from publicly available sources. Classification may be performed using, without limitation, linear classifiers such as without limitation logistic regression and/or naive Bayes classifiers, nearest neighbor classifiers such as k-nearest neighbors' classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(AB)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors' algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors' algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n}a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With continued reference to FIG. 1, classifier 140 may be configured to input psychiatric marker 108 to classifier 140 and output a probable psychiatric condition. A "probable psychiatric condition," as used in this disclosure, is a psychiatric disease and/or psychiatric condition that a user may current have and/or be at risk of developing in the future. For instance, and without limitation, classifier 140 may input a psychiatric marker 108 containing a subjective response indicating that a user has symptomatic complaints that include labile moods, marked irritability, lack of energy, overeating, and changes in eating habits to output a probable psychiatric condition such as premenstrual dysphoria disorder (PMDD). Computing device 104 may utilize a probable psychiatric condition to generate a nourishment program 128. For instance, and without limitation, a probable psychiatric condition such as obsessive-compulsive disorder may be utilized by computing device 104 to generate a nourishment program 128 that contains foods likely to stabilize a user's blood glucose and control mood swings and include meals that contain nuts, seeds, eggs, beans, meat, and complex carbohydrates. Classifier 140 may be configured to output a probable psychiatric condition containing a sub-condition expression. A "sub-condition expression," as used in this disclosure, is a sub-category of psychiatric disease and/or psychiatric conditions. A sub-category may include various types and/or categories of a psychiatric disease and/or psychiatric conditions which may be identified by certain traits, characteristics, symptoms, and/or psychiatric markers 108. For instance, and without limitation, a psychiatric disease such as bipolar disorder may contain sub-condition expressions such as Bipolar, I disorder, Bipolar II disorder, Cyclothymic disorder, and Bipolar disorder due to another medical or substance abuse disorder. In yet another non-limiting example, a psychiatric disease such as depression may contain sub-condition expressions such as clinical depression, persistent depressive disorder, postpartum depression, manic depression, depressive psychosis, premenstrual dysphoric disorder, seasonal depression, situational depression, and atypical depression.

With continued reference to FIG. 1, computing device 104 may be configured to identify an intervention assistance marker and modify the nourishment program as a function of the intervention assistance marker. Modification may be performed using any methodology as described above for generating nourishment program 128. For instance, and without limitation, modification may include removing nourishment possibilities, adding nourishment possibilities, and/or adjusting quantities and/or serving sizes of nourishment possibilities. An "intervention assistance marker," as used in this disclosure, is a treatment that a user may currently be using for the treatment and/or prevention of a psychiatric disease and/or psychiatric condition. A treatment may include a therapeutic agent, therapy, procedure, recommendation, product, technique, program, and the like that that may be utilized in the treatment and/or prevention of a psychiatric disease and/or psychiatric condition. A treatment may include but is not limited to prescription medications, supplements, over the counter medications, vitamins, minerals, herbal remedies, exercise programs, stress management techniques, acupuncture, massage therapy, group therapy, behavior therapy, and the like. For instance, and without limitation, an intervention assistance marker may indicate that a user has been recommended to engage in 150 minutes of cardiovascular exercise each week to aid a user in having an increased mood. In such an instance, computing device 104 may modify a nourishment program 128 to increase quantities of protein that a user is recommended to consume on days when the user engages in the cardiovascular exercise. In yet another non-limiting example, an intervention assistance marker may indicate that a user has been receiving massage treatments to aid in reducing the user's generalized anxiety disorder, whereby in such an instance computing device 104 may modify a nourishment program 128 to recommend foods containing extra hydration and electrolytes on days when the user receives a massage, including for example foods such as cucumber, tomatoes, oranges, and watermelon.

With continued reference to FIG. 1, computing device 104 may be configured to evaluate a user regarding a behavior marker and update a nourishment program 120 as a function of the behavior marker. Updating nourishment program 120 may be performed utilizing any methodology as described above for generating nourishment program 120. For instance, and without limitation, updating may include removing nourishment possibilities, adding nourishment possibilities, adjusting quantities and/or serving sizes of nourishment possibilities, adjusting recommended consumption time of nourishment possibilities and the like. A "behavior marker," as used in this disclosure, is conduct exhibited by a user. Conduct may include any worsening and/or easing of any symptoms over a certain period of time. For example, a behavior marker may indicate that a user experienced more frequent episodes of insomnia on nights when the user consumed dinner right before bedtime. Conduct may include any indicators of compliance with a nourishment program 128. For instance, and without limitation, a behavior marker may indicate that a user did not comply with a nourishment program for 3 days before experiencing increased symptoms of mania and panic. Conduct may also include any concerns that may be raised by family members, friends, caregivers and the like about a user. For instance, and without limitation, conduct may indicate a user's spouse has experienced lesser episodes of depression over the previous two weeks since consuming tryptophan containing foods. Computing device 104 may update a nourishment program 128 such as by adjusting ingredients, modifying meals, editing mealtimes and the like. For instance, and without limitation, a behavior marker that indicates a user experiences reduced episodes of premenstrual syndrome (PMS) when the user consumed foods high in indole-3-carbinol may be used by computing device 104 to update a nourishment program 128 to incorporate the foods high in indole-3-carbinol more frequently for the user. This may include updating nourishment program 128 to recommend foods such as broccoli, Brussel sprouts, cabbage, collards, cauliflower, kale, mustard greens, turnips, and rutabagas.

With continued reference to FIG. 1, computing device 104 may be configured to review a cognitive response of a user as a function of implementing a nourishment program 128. A "cognitive response," as used in this disclosure, is feedback from a user regarding a nourishment program 128. Feedback may include any information about how a user is doing in regard to a nourishment program 128. Feedback may include identifying what parts of a nourishment program 128 a user likes and enjoys implementing as well as what parts of a nourishment program 128 a user dislikes and seeks to modify. Feedback may also describe a user's current cognitive and/or mental state and may describe how a user feels and if a user feels that a user's psychiatric condition and/or psychiatric disease is better controlled and/or maintained. Computing device 104 may update a nourishment program 128 based on a cognitive response. Updating may be performed utilizing any methodology as described above in more detail.

Figure 2:
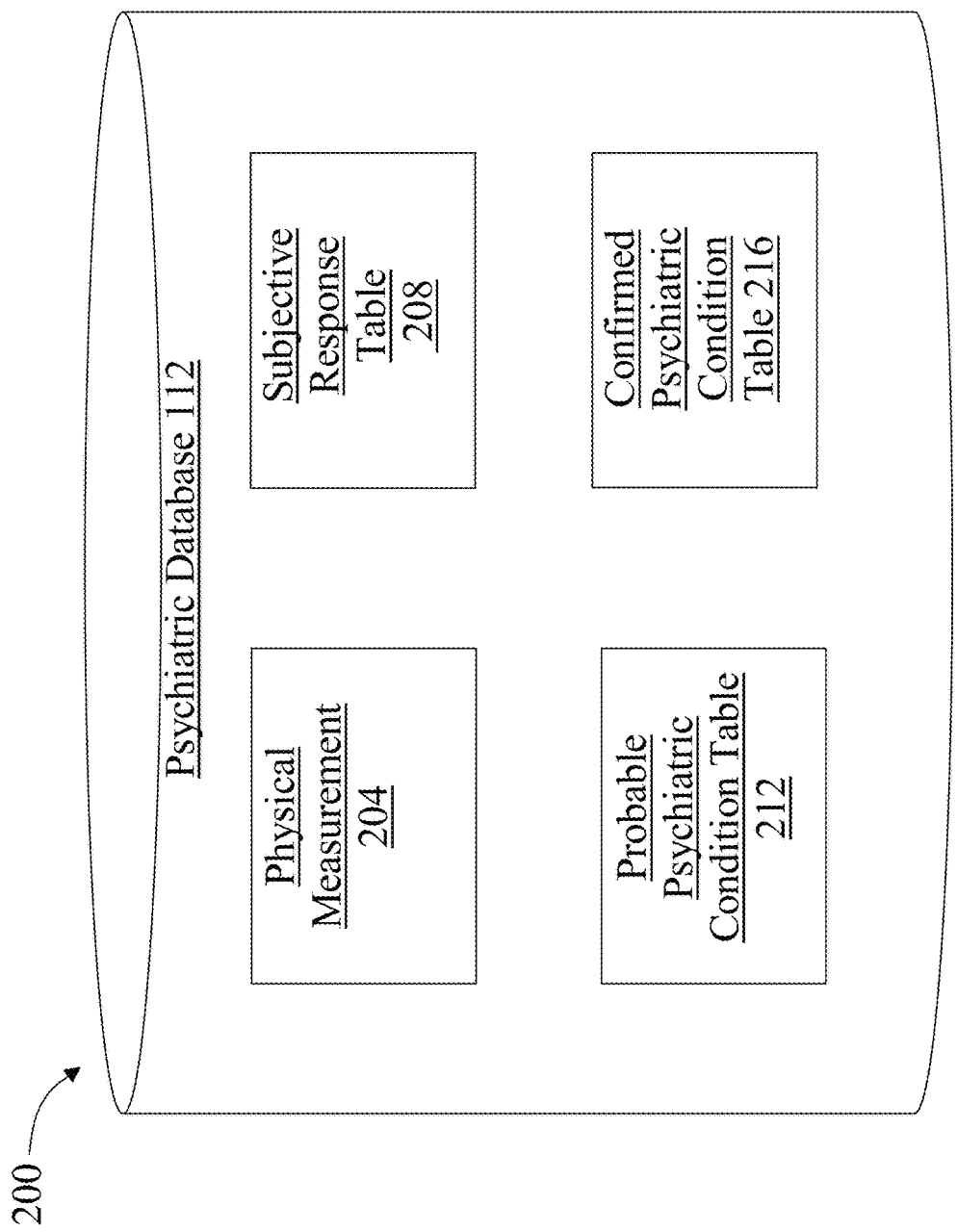
FIG. 2 is a block diagram illustrating an exemplary embodiment of a psychiatric database.

Referring now to FIG. 2, an exemplary embodiment 200 of a psychiatric database 112 is illustrated. Psychiatric database 112 may be implemented as any data structure as described above in more detail in reference to FIG. 1. One or more tables contained within psychiatric database 112 may include physical measurement table 204; physical measurement table 204 may include information relating to physical measurements. For instance, and without limitation, physical measurement table 204 may contain results from a saliva sample analyzed for one or more levels of hormones such as estradiol, estriol, estrone, progesterone, testosterone, cortisol, and dehydroepiandrosterone (DHEA). One or more tables contained within psychiatric database 112 may include subjective response table 208; subjective response table 208 may include information relating to subjective responses. For instance, and without limitation, subjective response table 208 may contain a user response containing a self-reported description of a user feeling upset during three of the last five days. One or more tables contained within psychiatric database 112 may include probable psychiatric condition table 212; probable psychiatric condition table 212 may include information relating to a probable psychiatric condition that may be generated by classifier 140. For instance, and without limitation, probable psychiatric condition table 212 may identify that a user is a risk of developing seasonal affective disorder. One or more tables contained within psychiatric database may include confirmed psychiatric condition table 216; confirmed psychiatric condition table 216 may identify any psychiatric conditions and/or psychiatric diseases that a user may have been diagnosed with by a medical professional, such as a doctor, nurse, physician assistant, and the like. For instance, and without limitation, confirmed psychiatric condition table 216 may indicate that a user was previously diagnosed by a doctor as having schizophrenia.

Figure 3:
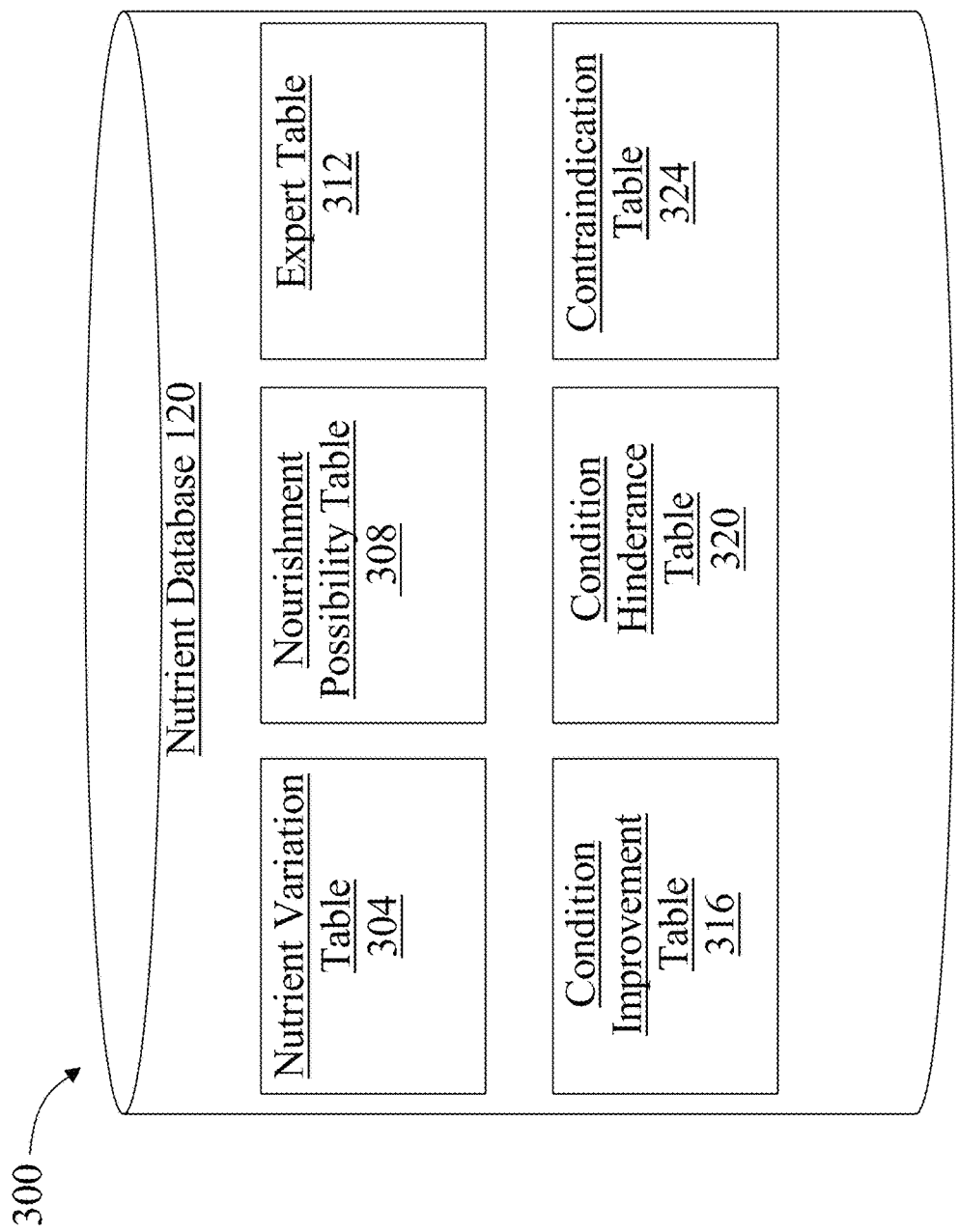
FIG. 3 is a block diagram illustrating an exemplary embodiment of a nutrient database.

Referring now to FIG. 3, an exemplary embodiment 300 of nutrient database 120 is illustrated. Nutrient database 120 may be implemented as any data structure suitable for use as psychiatric database as described above in more detail. One or more tables contained within nutrient database 120 may include nutrient variation table 304; nutrient variation table 304 may include any information relating to a nutrient variation 116. One or more tables contained within nutrient database 120 may include nourishment possibility table 308; nourishment possibility table 308 may include any information relating to nourishment possibilities 124. One or more tables contained within nutrient database 120 may include expert table 312; expert table 312 may include any inputs and/or entries relating to nutrient variation, nourishment possibilities, and the like generated by experts such as leading doctors, scientists, journal articles, publications, and the like. One or more tables contained within nutrient database 120 may include condition improvement table 316; condition improvement table 316 may include the identification of any substances and/or activities that improve a user's psychiatric condition and/or psychiatric disease. One or more tables contained within nutrient database 120 may include condition hinderance table 320; condition hinderance table 320 may include the identification of any substances and/or activities that hinder a user's psychiatric condition and/or psychiatric disease. One or more tables contained within nutrient database 120 may include contraindication table 324; contraindication table 324 may include any contraindicated foods and/or substances that a user may be prohibited from consuming.

Referring now to FIG. 4, an exemplary embodiment 400 of various psychiatric markers 108 is illustrated. Psychiatric markers 108 may include physical measurements 404, including any of the physical measurements 404 listed. Psychiatric markers 108 may include subjective responses 408, including any of the subjective responses 408 listed.

Referring now to FIG. 5, an exemplary embodiment 500 of nourishment possibilities is illustrated. In an embodiment, a psychiatric marker 108 may indicate that a user has low levels of serotonin. In such an instance, computing device 104 may identify nutrient variations 116 such as by locating ingredients and/or foods that contain serotonin boosting foods, such as for example, eggs, cheese, pineapple, tofu, salmon, and turkey. Computing device 104 may then evaluate various available nourishment possibilities 124. In an embodiment, nourishment possibilities 124 may be organized and/or sorted within nutrient database 120 by meal option, whereby nourishment possibilities 124 for breakfast 504 may be listed together, nourishment possibilities 124 for lunch 508 may be listed together, nourishment possibilities 124 for dinner 512 may be listed together, and nourishment possibilities 124 for snacks 516 may be listed together. Computing device 104 may select nourishment possibilities 124 and generate a nourishment program 128, whereby various meals for breakfast, lunch, dinner, and snacks may be chosen and selected.

Figure 6:
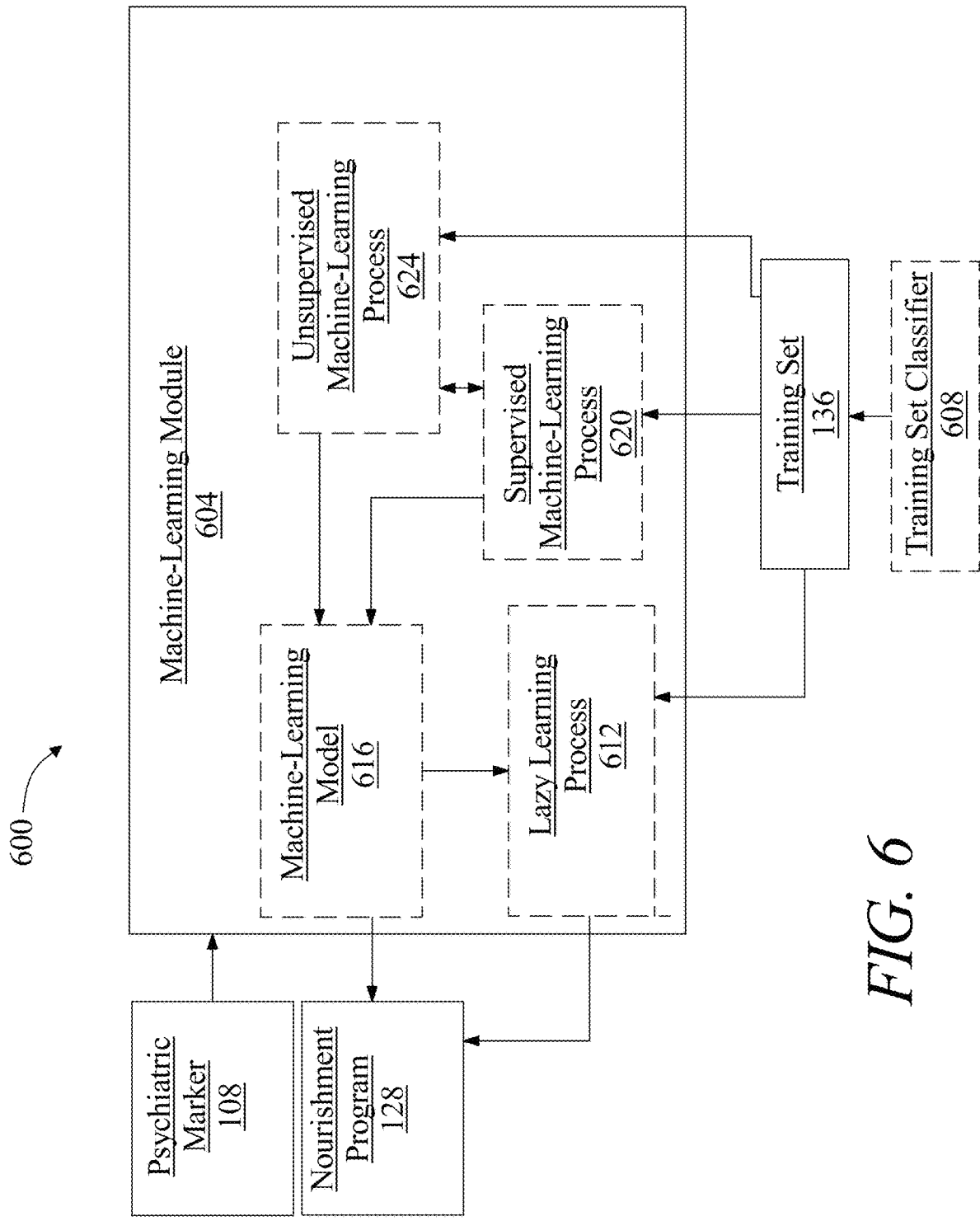
FIG. 6 is a diagrammatic representation of a machine learning module.

Referring now to FIG. 6, an exemplary embodiment 600 of a machine learning module 604 that may perform one or more machine learning processes as described in this disclosure is illustrated. Machine learning module may perform determinations, classification, and/or analysis steps, methods, processes, or the like as described in this disclosure using machine learning processes. Machine learning module may produce outputs such as nourishment programs 128 given data provided as inputs such as psychiatric markers 108; this is in contrast to a non-machine learning software program where the commands to be executed are determined in advance by a user and written in a programming language.

Further referring to FIG. 6, training set 136 may be filtered, sorted, and/or selected using one or more supervised and/or unsupervised machine learning processes and/or models as described in further detail below; such models may include without limitation a training data classifier 608. Training data classifier 608 may include a classifier, which is a machine learning model as defined above, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine learning module 604 may generate a classifier using a classification algorithm, defined as a process whereby a computing device and/or any module and/or component operating thereon derives a classifier from training data such as training set 136. Classification may be performed using, without limitation, linear classifiers such as without limitation logistic regression and/or naive Bayes classifiers, nearest neighbor classifiers such as k-nearest neighbors' classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 608 may classify elements of training data to a cohort of persons having a particular psychiatric disease and/or psychiatric condition such as bipolar disorder or schizophrenia.

Still referring to FIG. 6, machine learning module 604 may be configured to perform a lazy-learning process 612 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training set 136. Heuristic may include selecting some number of highest-ranking associations and/or training set elements. Lazy learning may implement any suitable lazy learning algorithm, including without limitation a K-nearest neighbors' algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine learning algorithms as described in further detail below.

Alternatively, or additionally, and with continued reference to FIG. 6, machine learning processes as described in this disclosure may be used to generate machine learning models 616. A "machine learning model," as used in this disclosure, is a mathematical and/or algorithmic representation of a relationship between inputs and outputs, as generated using any machine learning process including without limitation any process as described above and stored in memory; an input is submitted to a machine learning model 616 once created, which generates an output based on the relationship that was derived. For instance, and without limitation, a linear regression model, generated using a linear regression algorithm, may compute a linear combination of input data using coefficients derived during machine learning processes to calculate an output datum. As a further non-limiting example, a machine learning model 616 may be generated by creating an artificial neural network, such as a convolutional neural network comprising an input layer of nodes, one or more intermediate layers, and an output layer of nodes. Connections between nodes may be created via the process of "training" the network, in which elements from a training set 136 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 6, machine learning algorithms may include at least a supervised machine learning process 620. At least a supervised machine learning process 620, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include psychiatric markers 108 as described above as inputs, nourishment programs 128 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training set 136. Persons skilled in the art, upon reviewing the entirety of this disclosure, will be aware of various possible variations of at least a supervised machine learning process 620 that may be used to determine relation between inputs and outputs. Supervised machine learning processes may include classification algorithms as defined above.

Further referring to FIG. 6, machine learning processes may include at least an unsupervised machine learning process 624. An unsupervised machine learning process, as used herein, is a process that derives inferences in datasets without regard to labels; as a result, an unsupervised machine learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 6, machine learning module 604 may be designed and configured to create a machine learning model 616 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 6, machine learning algorithms may include, without limitation, linear discriminant analysis. Machine learning algorithm may include quadratic discriminate analysis. Machine learning algorithms may include kernel ridge regression. Machine learning algorithms may include support vector machines, including without limitation support vector classification-based regression processes. Machine learning algorithms may include stochastic gradient descent algorithms, including classification and regression algorithms based on stochastic gradient descent. Machine learning algorithms may include nearest neighbors' algorithms. Machine learning algorithms may include Gaussian processes such as Gaussian Process Regression. Machine learning algorithms may include cross-decomposition algorithms, including partial least squares and/or canonical correlation analysis. Machine learning algorithms may include naïve Bayes methods. Machine learning algorithms may include algorithms based on decision trees, such as decision tree classification or regression algorithms. Machine learning algorithms may include ensemble methods such as bagging meta-estimator, forest of randomized tress, AdaBoost, gradient tree boosting, and/or voting classifier methods. Machine learning algorithms may include neural net algorithms, including convolutional neural net processes.

Figure 7:
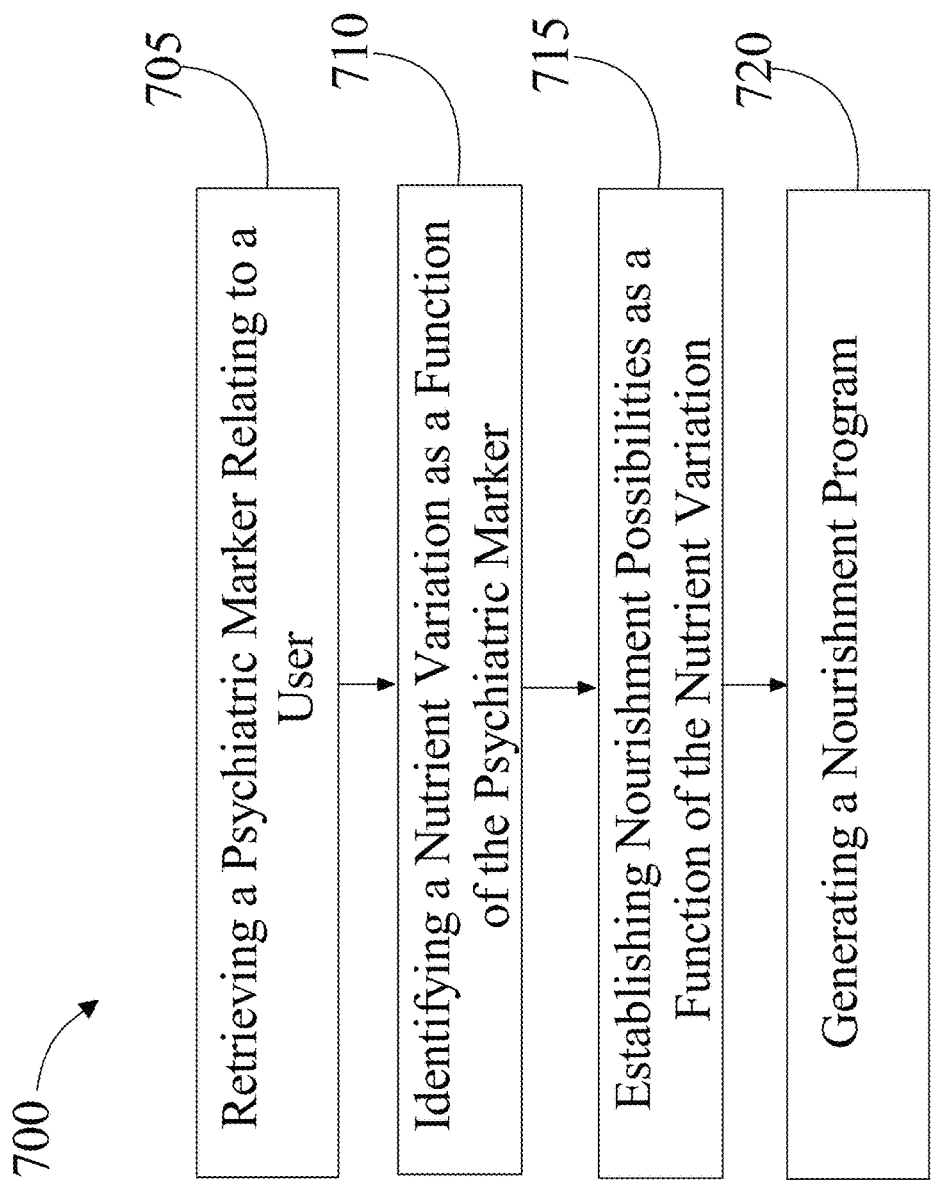
FIG. 7 is a flow diagram illustrating an exemplary embodiment of a method of nourishment refinement using psychiatric markers.

Referring now to FIG. 7, an exemplary embodiment of a method 700 of nourishment refinement using psychiatric markers is illustrated. At step 705, a computing device 104 retrieves a psychiatric marker 108 relating to a user. A psychiatric marker 108 includes any of the psychiatric markers 108 as described above in more detail in reference to FIGS. 1-6. Computing device 104 may retrieve a psychiatric marker 108 from psychiatric database 112. A psychiatric marker 108 may include a physical measurement, including any of the physical measurements as described above in more detail in reference to FIGS. 1-6. For instance, and without limitation, a psychiatric marker 108 may include a urinary level of dopamine. In yet another non-limiting example, a psychiatric marker 108 may include results from a medical procedure and/or assessment such as findings from magnetic resonance imaging (MM).

With continued reference to FIG. 7, at step 710, computing device 104 identifies a nutrient variation 116 as a function of a psychiatric marker 108. A nutrient variation 116 includes any of the nutrient variations 116 as described above in more detail in reference to FIGS. 1-6. A nutrient variation may include a list of one or more nutrients that may require customization and/or optimization based on a psychiatric marker 108. For instance, and without limitation, a psychiatric marker 108 such as a high salivary level of testosterone in a female may be utilized by computing device 104 to identify nutrient variations 116 that include nuts, wild salmon, green tea, red rishi mushrooms, and flaxseed. Information pertaining to a nutrient variation 116 may be contained within nutrient database 120. Identifying a nutrient variation 116 includes determining a degree of psychiatric impairment. This may be performed utilizing any methodologies as described above in more detail in reference to FIG. 1. Computing device 104 may identify a nutrient variation 116 by determining a psychiatric variation element which may alter and/or affect a person's psychiatric state. For instance, and without limitation, a psychiatric variation element such as a B vitamin supplement may be identified as a substance a user is currently consuming. Computing device 104 may identify a nutrient variation 116 using a psychiatric variation element. For instance, and without limitation, a psychiatric variation element that indicates a user is consuming a zinc supplement may be utilized by computing device 104 to identify a nutrient variation 116 to ensure that a user consumes adequate quantities of copper, because zinc supplementation may deplete copper quantities in the human body. Information pertaining to a nutrient variation 116 may be stored within nutrient database 120.

With continued reference to FIG. 7, at step 715, computing device 104 establishes nourishment possibilities 124 as a function of a nutrient variation 116 and a degree of psychiatric impairment. Nourishment possibilities 124 include any of the nourishment possibilities as described above in more detail in reference to FIGS. 1-6. Nourishment possibilities 124 may identify one or more meals that comply with a nutrient variation 116. For instance, and without limitation, a nutrient variation 116 that identifies nutrients such as additional B vitamins that are required for a user may be utilized to establish nourishment possibilities 124 that contain foods high in B vitamins such as wholegrain bread, fortified cereal, and bananas. Computing device 104 may establish nourishment possibilities 124 by generating a query relating to a psychiatric marker 108 and a nutrient variation 116 and establishing nourishment possibilities 124 by generating the query. This may be performed using any of the methodologies as described above in more detail in reference to FIGS. 1-6. For instance, and without limitation, a psychiatric marker 108 containing a subjective response indicating a user is experiencing a depressed mood and low in energy may be utilized by computing device 104 to generate a query to locate nourishment possibilities 124 that contain foods high in serotonin promoting foods such as oatmeal, salmon, and pineapple. In yet another non-limiting example, a degree of psychiatric impairment that indicates a user is institutionalized and undergoing intense psychiatric treatments may be utilized to select nourishment possibilities 124 that can be administered and/or delivered to the user while in the psychiatric institution, such as by creating options that can be delivered through aa nasogastric tube, a nasojejunal tube, and/or delivered through total parenteral nutrition (TPN) and the like.

With continued reference to FIG. 7, at step 720, computing device 104 generates a nourishment program 128. Nourishment program 128 includes any of the nourishment programs as described above in more detail in reference to FIGS. 1-6. Nourishment program 128 may include an eating plan intended to treat, prevent, reverse, and/or cure psychiatric a psychiatric condition and/or a psychiatric disease. Nourishment program 128 may specify recommended and/or assigned meals on specific days of the week. Nourishment program 128 may also include information describing recommended times of the day when certain meals should be consumed. Nourishment program 128 may be generated by training a machine learning process 132 using a training set 136 relating psychiatric markers and nutrient variations to nourishment programs. Computing device 104 may generate a nourishment program as a function of a psychiatric marker 108, nourishment possibilities 124 and a machine learning process 132. This may be performed utilizing any of the methodologies as described above in more detail in reference to FIGS. 1-6.

With continued reference to FIG. 7, computing device 104 may input a psychiatric marker 108 to a classifier 140, wherein the classifier 140 inputs psychiatric markers 108 and outputs probable psychiatric conditions using a classification process. This may be performed using any of the methodologies as described above in more detail in reference to FIGS. 1-6. Classifier 140 outputs a probable psychiatric condition, including any of the probable psychiatric conditions as described above in more detail in reference to FIGS. 1-6. A probable psychiatric condition may include a psychiatric disease and/or psychiatric condition that a user may current have and/or be at risk of developing in the future. For instance, and without limitation, a psychiatric marker 108 such as a mutation of the 5-HTTLPR and Stin2 VNTR genes may indicate that a user is at risk of developing postpartum depression, using classifier 140. Computing device 104 generates a nourishment program 128 using the probable psychiatric condition as described above in more detail in reference to FIGS. 1-6. In an embodiment, a probable psychiatric condition may include a sub-condition expression, including any of the sub-condition expressions as described above in more detail in reference to FIGS. 1-6. For instance, and without limitation, a probable psychiatric condition such as eating disorders may include sub-condition expressions such as anorexia nervosa, bulimia nervosa, binge eating disorder, pica, rumination disorder, avoidant/restrictive food intake disorder, purging disorder, night eating syndrome, and/or other specified feeding or eating disorder (OSFED).

With continued reference to FIG. 7, computing device 104 may modify a nourishment program 128 using an intervention assistance marker. An intervention assistance marker may include treatment that a user may currently be using for the treatment and/or prevention of a psychiatric disease and/or psychiatric condition. For instance, and without limitation, an intervention assistance marker may indicate that a user is currently taking a prescription medication such as lithium carbonate. In such an instance, computing device 104 may modify nourishment program 128 to guard against lithium toxicity such as by ensuring nourishment program 128 contains stable quantities of sale and caffeine. Computing device 104 may evaluate a user regarding a behavior marker and update a nourishment program 128 based on the behavior marker. A behavior marker may include and describe a user's conduct over time and/or any worsening or improvement of symptoms. For example, a behavior marker may indicate that a user experiences better symptomatic control of anxiety issues when following nourishment program 128. In yet another non-limiting example, a behavior marker may indicate that a user experiences a worsening of memory problems and fatigue when the user doesn't follow the recommended mealtimes contained within a nourishment program 128 and instead eats at times the user prefers. Computing device 104 may review a cognitive response of a user as a function of implementing a nourishment program 128 and update the nourishment program 128 using the cognitive response. For instance, and without limitation, a cognitive response may indicate that a user did not enjoy a particular meal such as the breakfast option containing a tofu scramble with whole wheat toast, but the user did enjoy a breakfast option containing a granola parfait with gluten free granola and fresh berries. In such an instance, computing device 104 may update nourishment program 128 to eliminate breakfast options containing the tofu scramble and instead substitute a more compatible breakfast option.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
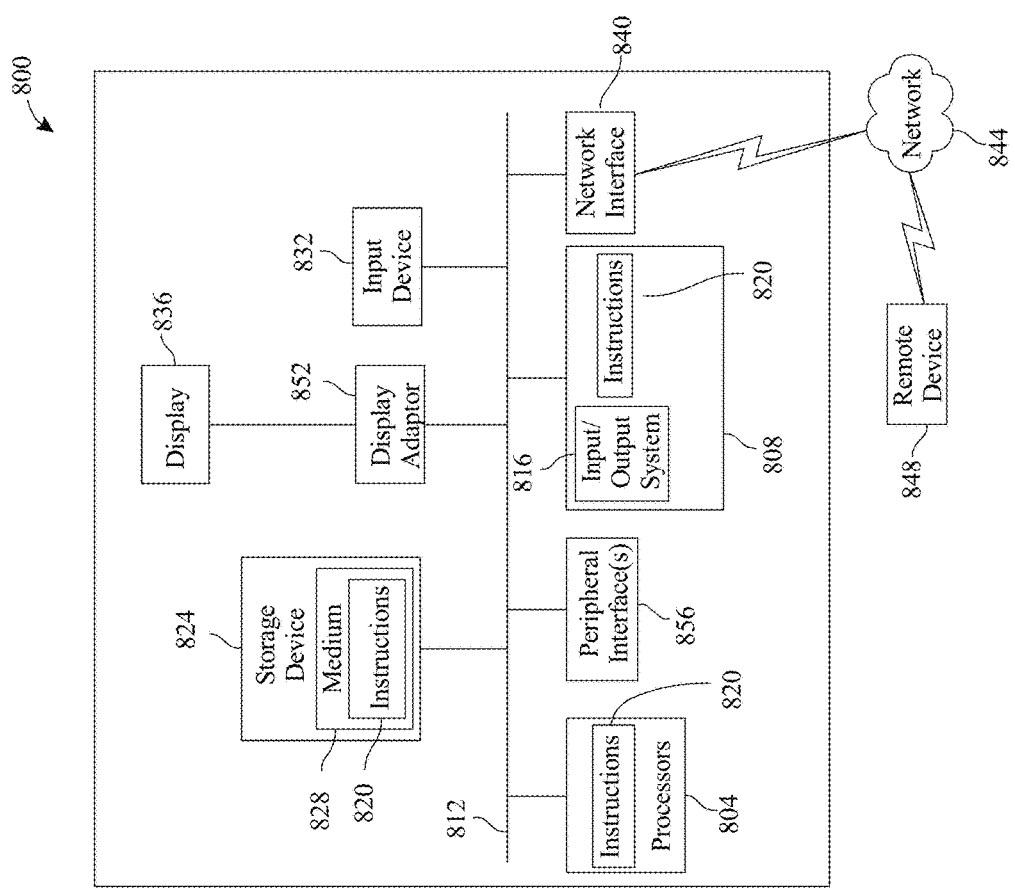
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for nourishment refinement using psychiatric markers, the system comprising:
    a computing device designed and configured to:
        retrieve a psychiatric marker relating to a user, wherein the psychiatric marker is an indicator of a psychiatric condition of the user; wherein the psychiatric condition includes a gambling addiction disorder;

input the psychiatric marker to a classifier, the classifier configured to input psychiatric markers and output a sub-condition expression, wherein the classifier is generated by executing a classification process;
output a sub-condition expression;
generate the nourishment program as a function of the sub-condition expression;
identify a nutrient variation as a function of the psychiatric marker and a degree of psychiatric impairment, wherein the degree of psychiatric impairment indicates a severity of a psychiatric condition indicated by the psychiatric marker, wherein the degree of psychiatric impairment is determined as a function of a machine learning process, the machine learning process configured to be trained using a training data, where the training data comprises correlations of psychiatric markers to degrees of psychiatric impairment;
establish nourishment possibilities as a function of the nutrient variation and the degree of psychiatric impairment, wherein establishing the nourishment possibilities further comprises:
generating a query relating to the psychiatric marker and the nutrient variation; and
establishing the nourishment possibilities as a function of the query; and
generate a nourishment program, wherein generating further comprises:
training a machine learning process as a function of a training set relating psychiatric markers and nutrient variations to nourishment programs;
inputting the psychiatric marker into the machine learning process;
outputting, using the machine learning process, the nourishment program as a function of the machine learning process and the psychiatric marker;
receiving a cognitive response from the user, wherein the cognitive response comprises:
a first feedback including an identification of parts of the nourishment program the user:
likes and wishes to implement; and
dislikes and wishes to modify; and
a second feedback including a current cognitive and mental state of the user including how the user currently feels on a current status of the gambling addiction disorder of the user; and
updating the nourishment program as a function of the nourishment possibilities and the cognitive response.

2. The system of claim 1, wherein the psychiatric marker further comprises a physical measurement.

3. The system of claim 1, wherein the psychiatric marker further comprises a subjective response.

4. The system of claim 1, wherein the computing device is further configured to:
determine a psychiatric variation element consumed by the user; and
identify the nutrient variation as a function of the psychiatric variation element.

5. The system of claim 1, wherein the computing device is further configured to:
identify an intervention assistance marker used by the user; and
modify the nourishment program as a function of the intervention assistance marker.

6. The system of claim 1, wherein the computing device is further configured to:
evaluate the user regarding a behavior marker; and
update the nourishment program as a function of the behavior marker.

7. The system of claim 1, wherein the computing device is further configured to review the cognitive response of the user as a function of implementing the nourishment program.

8. The system of claim 1, wherein the degree of psychiatric impairment comprises a severity score.

9. A method of nourishment refinement using psychiatric markers, the method comprising:
retrieving, by a computing device, a psychiatric marker relating to a user, wherein the psychiatric marker is an indicator of a psychiatric condition of the user; wherein the psychiatric condition includes a gambling addiction disorder;
inputting, by the computing device, the psychiatric marker to a classifier, the classifier configured to input psychiatric markers and output a sub-condition expression, wherein the classifier is generated by executing a classification process;
outputting, by the computing device, a sub-condition expression;
generating the nourishment program as a function of the sub-condition expression;
identifying, by the computing device, a nutrient variation as a function of the psychiatric marker and a degree of psychiatric impairment, wherein the degree of psychiatric impairment indicates a severity of a psychiatric condition indicated by the psychiatric marker, wherein the degree of psychiatric impairment is determined as a function of a machine learning process, the machine learning process configured to be trained using a training data, where the training data comprises correlations of psychiatric markers to degrees of psychiatric impairment;
establishing, by the computing device, nourishment possibilities as a function of the nutrient variation and the degree of psychiatric impairment, wherein establishing the nourishment possibilities further comprises:
generating a query relating to the psychiatric marker and the nutrient variation; and
establishing the nourishment possibilities as a function of the query; and
generating, by the computing device, a nourishment program, wherein generating further comprises:
training a machine learning process as a function of a training set relating psychiatric markers and nutrient variations to nourishment programs;
inputting the psychiatric marker into the machine learning process;
outputting, using the machine learning process, the nourishment program as a function of the machine learning process and the psychiatric marker;
receiving a cognitive response from the user, wherein the cognitive response comprises:
a first feedback including an identification of parts of the nourishment program the user:
likes and wishes to implement; and
dislikes and wishes to modify; and
a second feedback including a current cognitive and mental state of the user including how the user currently feels on a current status of the gambling addiction disorder of the user; and
updating the nourishment program as a function of the nourishment possibilities and the cognitive response.

10. The method of claim 9, wherein the psychiatric marker further comprises a physical measurement.

11. The method of claim 9, wherein the psychiatric marker further comprises a subjective response.

12. The method of claim 9, wherein identifying the nutrient variation further comprises:
   determining a psychiatric variation element consumed by the user; and
   identifying the nutrient variation as a function of the psychiatric variation element.

13. The method of claim 9, wherein generating the nourishment program further comprises:
   identifying an intervention assistance marker used by the user; and
   modifying the nourishment program as a function of the intervention assistance marker.

14. The method of claim 9, wherein generating the nourishment program further comprises:
   evaluating the user regarding a behavior marker; and
   updating the nourishment program as a function of the behavior marker.

15. The method of claim 9 further comprising reviewing the cognitive response of the user as a function of implementing the nourishment program.

16. The method of claim 9, wherein the degree of psychiatric impairment comprises a severity score.

* * * * *